United States Patent
Welshimer et al.

(10) Patent No.: US 10,577,281 B1
(45) Date of Patent: Mar. 3, 2020

(54) NON-DISPERSIBLE GRANULAR SUBSTRATE

(71) Applicant: The National Lime and Stone Company, Findlay, OH (US)

(72) Inventors: James Welshimer, Findlay, OH (US); Jeffrey Wigdahl, Findlay, OH (US)

(73) Assignee: The National Lime and Stone Company, Findlay, OH (US)

( * ) Notice: Subject to any disclaimer, the term of this patent is extended or adjusted under 35 U.S.C. 154(b) by 191 days.

(21) Appl. No.: 15/229,183

(22) Filed: Aug. 5, 2016

Related U.S. Application Data

(60) Provisional application No. 62/202,209, filed on Aug. 7, 2015.

(51) Int. Cl.
| | |
|---|---|
| *C04B 28/04* | (2006.01) |
| *C04B 14/28* | (2006.01) |
| *C04B 14/18* | (2006.01) |
| *C04B 16/02* | (2006.01) |
| *A01N 25/12* | (2006.01) |
| *A01K 1/015* | (2006.01) |

(52) U.S. Cl.
CPC ............ *C04B 28/04* (2013.01); *A01K 1/0154* (2013.01); *A01N 25/12* (2013.01); *C04B 14/18* (2013.01); *C04B 14/28* (2013.01); *C04B 16/02* (2013.01)

(58) Field of Classification Search
CPC ......... C04B 28/04; C04B 14/18; C04B 14/28; C04B 16/02; A01K 1/015; A01N 25/12
See application file for complete search history.

(56) References Cited

U.S. PATENT DOCUMENTS

| | | | | |
|---|---|---|---|---|
| 4,011,061 A | * | 3/1977 | Forseen | C05G 3/0017 424/405 |
| 6,080,234 A | * | 6/2000 | Clavaud | C04B 28/02 106/640 |
| 6,231,660 B1 | * | 5/2001 | Welshimer | A01N 25/14 106/405 |
| 6,613,138 B2 | * | 9/2003 | Welshimer | A01N 25/14 106/405 |
| 7,563,424 B2 | * | 7/2009 | Scranton et al. | B01D 53/02 423/244.06 |
| 2002/0073898 A1 | * | 6/2002 | Schelinski | C03C 11/007 106/675 |
| 2007/0244681 A1 | * | 10/2007 | Cohen | E21B 43/25 703/10 |
| 2013/0289168 A1 | * | 10/2013 | Zember | C04B 28/02 524/5 |

OTHER PUBLICATIONS

America's Cement Manufacturers since 2017.*

* cited by examiner

*Primary Examiner* — Blessing M Fubara
(74) *Attorney, Agent, or Firm* — Marshall & Melhorn, LLC

(57) ABSTRACT

A non-dispersible granular substrate is formed of a plurality of granules, each granule being a mixture including an inert mineral component, a mineral cement, and optionally a light weight additive. The granular substrate could be used, for example, as carriers for pesticides or soil amendments, and as animal bedding (e.g. cat litter). A method of making a non-dispersible granular substrate includes forming a batch mixture including an inert mineral component, a mineral cement, and water, and co-pelletizing the batch mixture to form a plurality of non-dispersible granules.

23 Claims, No Drawings

NON-DISPERSIBLE GRANULAR SUBSTRATE

BACKGROUND OF THE INVENTION

The invention relates to granular materials used as carriers for pesticides, soil amendments, and as animal bedding (e.g. cat litter). Such granular materials are typically 1 to 1.5 millimeters in average particle size (approx. US mesh 8×16), with a bulk density less than 65 pounds per cubic foot (pcf) and with an RTA (weight % resistance to attrition) of at least 85%.

Granular materials formed by agglomeration of powdered ingredients often use organic polymers to bind the fine ingredient particles into granules. The resulting granules or pellets may be dispersible or non-dispersible depending on the properties of the organic polymer binder agent.

There can be adverse reactions between the organic polymer binders and "active agents." Water borne active agents may partially dissolve water dispersible granules or may result in storage stability issues (mold formation) in non-dispersible granules. Organic solvents used to dissolve active agents may also attack the organic polymer binders degrading granule strength characteristics.

Granular material may also be formed by agglomerating fibrous particles with powdered mineral components. In this case the agglomeration process forms granules by enabling the fibrous particles to "knit together." Granules formed by this process are generally not as durable as granules produced with organic polymer binders.

Granular materials formed by agglomeration with organic polymer binders or by "knitting together" of fibrous materials use water as an essential ingredient to effect granulation, and this water must be driven off in a dryer to complete the agglomeration process. The residual water content in the granules following agglomeration is often described as "green pellet moisture." Removal of "green pellet moisture" by drying accounts for a significant proportion of the energy required for production of these types of granules.

SUMMARY OF THE INVENTION

A non-dispersible granular substrate is formed of a plurality of granules, each granule being a mixture including an inert mineral component, a mineral cement, and optionally a light weight additive. The granular substrate could be used, for example, as carriers for pesticides or soil amendments, and as animal bedding (e.g. cat litter). A method of making a non-dispersible granular substrate includes forming a batch mixture including an inert mineral component, a mineral cement, and water, and co-pelletizing the batch mixture to form a plurality of non-dispersible granules.

DESCRIPTION OF THE INVENTION

It is to be understood that the invention may assume various alternative orientations and step sequences, except where expressly specified to the contrary. It is also to be understood that the specific materials and processes described in the following specification are simply exemplary embodiments of the inventive concepts defined in the appended claims. Hence, specific dimensions, directions or other physical characteristics relating to the embodiments disclosed are not to be considered as limiting, unless the claims expressly state otherwise.

The invention overcomes the shortcomings described above by using a mineral cement as the binding agent. The resulting granules are inert and non-dispersible. Water dispersibility was tested by placing about 10 grams of the granular substrate into 100 ml of water at room temperature in a ~250 ml closed clear glass container. After one minute, the container was inverted and the time was observed until the granular material completely dispersed. The granules of the present invention showed no disintegration after 5 minutes following inversion. They are essentially non-dispersible.

The granules of the invention also preferably are light weight, have reduced incidence of adverse reaction with water or solvent borne active agents, show high liquid absorption capacity, show excellent storage stability, and show high strength, typically better strength than pellets formed by the "knitting together" of fibrous material. It appears that the granules formed using mineral cement binder in accordance with the invention utilize some the "green pellet moisture" to activate the mineral cement to bring about the binding action there by reducing the energy required for drying once the agglomeration is complete.

It is to be understood that the specific devices and processes described herein are simply exemplary embodiments of the inventive concepts. Hence, specific dimensions and other physical characteristics relating to the embodiments disclosed herein should not be considered as limiting, unless the claims expressly state otherwise. Unless stated otherwise, all percentages expressed herein are by weight.

In accordance with the invention, a granular material or granular substrate includes one or more inert mineral components, one or more mineral cements, water, and (optionally) one or more light weight additives, which may be included to reduce bulk density of the granules. These components are agglomerated using a pin mixer and pan or other conventional agglomeration equipment and processes.

The moisture required to effect granulation is retained in the granules to activate (hydrate) the mineral cement. The mineral cement will "cure," or develop strength over time. Chemical additives may be included in the formulation and/or heating may be included in the process to reduce the time needed for the mineral cement to cure. Once the mineral cement has attained sufficient strength, the granules may be dried and screened to the desired particle size distribution using conventional minerals processing equipment.

The one or more inert mineral components may be formed of any suitable inert mineral material, including dolomite, limestone, ground recycled concrete, ground air cooled blast furnace slag, or other inert mineral powders suitable for use with hydraulic mineral cements. The one or more inert mineral components preferably include dolomite or limestone, with dolomite being most preferred.

The one or more inert mineral components are preferably 30% to 85% of the final granular substrate composition. The one or more inert mineral components preferably are inert mineral powders having bulk density greater than about 70 pcf with a particle sizing of about 100% passing 30 mesh and about 10% or more passing 200 mesh. Particle size of about 100% passing US 30 mesh, 70% to 95% passing 100 mesh, and 35% to 75% passing the 200 mesh sieve is most preferable.

The one or more mineral cements (or hydraulic mineral cements) useful in accordance with the invention are materials derived from minerals which react when exposed to moisture (i.e., hydrate) to form crystal structures which bind the inert mineral particles and any optional light weight additive particles into solid granules. The one or more mineral cements of the invention are typically powdery substances made with calcined lime and clay, and may include Portland cement, finely ground Portland cement clinker, cement kiln dust (CKD), Portland cement blends (which are made by blending cementitious materials such as ground granulated blast furnace slag, fly ash, volcanic ash, or silica fume with Portland cement), and rapid-hardening hydraulic cements (e.g. calcium fluoroaluminate or calcium sulfoaluminate cements). Portland cement meeting the requirements spelled out in ASTM C150 is preferred, with Type III (High Early Strength) Portland cement being most preferred.

The one or more mineral cements preferably account for 15% to 42% of the final granular substrate composition.

The inclusion of one or more light weight additives in the batch for forming the granular substrates of the invention is optional, depending largely on the bulk density desired of the resulting granules. Accordingly, the granules of the invention may include one or more light weight additives amounting to from 0% to 35% of the final granular substrate composition.

The one or more light weight additives are preferably dry, powder materials having a bulk density less than 35 pcf and preferably having a sizing of about 100% passing a 20 mesh sieve and about 50% or more passing a 40 mesh sieve.

Suitable light weight additives include particle board flour, expanded silica, perlite, wood flour, cellulose, ground wheat straw, diatomaceous earth, and other materials meeting the particle size and bulk density properties would also be suitable. Particle board flour and hard wood flour are preferred materials for the light weight additive, with a particle board flour or hard wood flour having a sizing of 95% or more passing US 40 mesh sieve being most preferred.

In addition to the one or more inert mineral components, one or more mineral cements, water, and optional one or more light weight additive(s), the granular substrates of the invention may also optionally be formed with other additives, such as chemical additives to enhance the hydration rate and hasten strength gain for the mineral cement. In an embodiment, calcium chloride is included at about 3% of the granular substrate composition. While calcium chloride contributes to rapid strength development in the granules, its presence also makes the granules more hygroscopic than they would otherwise be, which can result in undesirable moisture absorption when the granular substrate is stored in bulk stockpiles (out of the weather but exposed to ambient atmosphere).

The granular material of the invention is non-dispersible in water and the bulk density of the granules can vary significantly to suit the desired application depending in large part on the amount of light weight additive included in the formulation. The bulk density of the granules is preferably 75 pounds per cubic foot ("pcf") or less, and more preferably between 25 and 75 pcf. In an embodiment, the granules have a high bulk density of 60-75 pcf. In another embodiment, the granules have a medium bulk density of 45-60 pcf. In a further embodiment, the granules have a low bulk density o 35-45 pcf. In still another embodiment, the weight % of light weight additive is increased to the point that the granules have a very low bulk density of 25-35 pcf.

For the high bulk density granules of the invention, the bulk density of the granules is from 60 to 75 pcf, and is most preferably about 65 pcf. Granules in accordance with this embodiment preferably include one or more inert mineral components at 70% to 85%, most preferably about 80%, mineral cement at 15% to 25%, most preferably about 20%, and one or more light weight additives at 0% to 2%, most preferably 0%.

For the medium bulk density granules of the invention, the bulk density of the granules is from 45 to 60 pcf, most preferably about 50 pcf. Granules in accordance with this embodiment preferably include one or more inert mineral components at 50% to 70%, most preferably about 55%, mineral cement at 20% to 35%, most preferably about 30%, and one or more light weight additives at 10% to 25%, most preferably about 15%.

For the low bulk density granules of the invention, the bulk density of the granules is from 35 to 45 pcf, most preferably about 40 pcf. Granules in accordance with this embodiment preferably include one or more inert mineral components at 40% to 55%, most preferably about 45%, mineral cement at 25% to 38%, most preferably about 35%, and one or more light weight additives at 15% to 30%, most preferably about 20%.

For the very low bulk density granules of the invention, the bulk density of the granules is from 25 to 35 pcf, most preferably about 30 pcf. Granules in accordance with this embodiment preferably include one or more inert mineral components at 30% to 46%, most preferably about 38%, mineral cement at 30% to 42%, most preferably about 38%, and one or more light weight additives at 20% to 35%, most preferably about 24%.

In certain embodiments of the invention, the granular substrates preferably exhibit an RTA of 85% or more, and most preferably 95% or more, in accordance with ASTM E 728-91 Volume 11.04, a most preferred particle size distribution of 6×60 mesh with 8×20 mesh being most preferable, virtually no dispersibility in water, a liquid absorption capacity of 10% or more, a pH of 7 to 10, a moisture content of at most 6%, with a maximum 1.5% being most preferred, and an angle of repose of 40° maximum, with 35° or lower being most preferred. The angle of repose of a granular material is the steepest angle of incline relative to the horizontal plane to which a material can be piled without slumping.

EXAMPLES

Table I shows the recipe for 4 trial batches prepared in the laboratory.

For each of the four trial batches, the dry ingredients were thoroughly blended and then added to the "initial solution" with mechanical mixing sufficient to wet and thoroughly blend all the ingredients within 5 seconds. This mixing was completed in the laboratory with a hand mixer fitted with traditional "flat blade" metal beaters and ~2 quart stainless steel mixing bowl. This procedure simulated initial mixing in a commercial pin mixer.

Following the initial blending of ingredients and the water solution, granulation continued in the same bowl, using a hand mixer with spiral wire beaters and fine water spray added from a hand held spray bottle, until a majority of the particles attained the desired size, which in these trial batches was approximately 10×16 mesh. It should be noted that the speed of the mixer can be adjusted to effect granule properties; that is, higher speeds result in smaller, higher bulk density granules. This procedure further simulated the granulation which would occur in a commercial pin mixer.

Following granulation with the hand mixer, the entire batch was tumbled for approximately one minute (~25 revolutions) in a 16 inch diameter by 3.5 inch deep pelletizing pan (inclined at 45° above horizontal) to improve the roundness of the granules and provide a better estimate of granule properties if the granules would be produced in a commercial pin mixer/pelletizing pan process.

Following granulation and initial bulk density determination, each batch was stored in sealed container(s), maintained at room temperature (except for trial batch 5D), and then sampled for moisture content and RTA. It should be noted that the moisture content dropped as the wet curing time was extended. While not wishing to be bound by any particular theory, it is suspected that the mineral cement is reacting with some portion of the moisture (i.e., hydrating) to form crystals which bind the ingredients and impart strength to each of the particles.

As used herein, PC stands for Portland cement and PBF stands for particle board flour, pcf stands for pounds per cubic foot, and UOM stands for units of measure.

TABLE I

Granular Material - Mineral Cement Test Batches Prepared in Laboratory

| | | | | Trial Batch Number | | | |
|---|---|---|---|---|---|---|---|
| | | | | A | 5D | B | C |
| | | | | Weight % for each ingredient in finished, dry pellets | | | |
| | | | UOM | PC 20% CaCL2 0.64% #60 80% | PC 20% #60 80% | PC 34.5% CaCL2 2.8% PBF 14.8% #60 47.9% | PC 34.5% CaCL2 2.8% PBF 14.8% #60 47.9% |
| TEST BATCH RECIPE | Dry, powdered ingredients (thoroughly blended prior to pelletizing) | Type III Portland Cement | Grams | 120 | — | 210 | 210 |
| | | Type I Portland Cement | Grams | — | 160 | | |
| | | #60 Dried Dolomite (~90% pass 100M; ~65% pass 200M) | Grams | 480 | 640 | 291 | 283 |
| | | Particle Board Flour (~100% pass 40M; ~30% pass 200M) | Grams | — | — | 90 | 90 |
| | Initial solution blended rapidly with the dry ingedients | Water | Grams | 60 | 50 | 49 | 100 |
| | | CaCl2 solution (32% solids) (Grams mixed with initial water addition) | Grams | 12 | | 52.6 | 52.5 |
| | Additional moisture (added as a fine spray) to bring about larger granules in the granulation stage (10 × 16 mesh target size)) | Granulation water | Grams | 30 | 86.3 | 130 | 57.4 |
| Moisture Content for Granules Immediately Following Granulation (Calculated) | | | % | 15 | 14.7 | 26 | 24 |
| Bulk Density for Granules Immediately Following Granulation | | | pcf | 65 | — | 41.8 | 43.8 |

Further properties for granules made in trial batches A, 5D, B, and C are set forth below. It is noted that all granules were dried at 240 F prior to testing, that trial batches A and 5D did not contain any light weight additive; and that trial batches B and C both contained PBF.

For trial batch A, after 5 days wet curing time at room temperature and drying at 240 F, moisture loss in the granules was 9.5% (compared to an estimated moisture content of 15% following granulation). The 10×16 mesh granules were collected by sieving and showed RTA value of 97.4% and Bulk Density value of 65 pcf.

For trial batch 5D, half the granules were wet cured at room temperature and half were wet cured at 100 F.

For the half of trial batch 5D cured wet for 3 days at room temperature and then dried at 240 F, moisture loss in the granules was 11.3% (compared to an estimated moisture content of 14.7% following granulation). RTA for the 10×16 mesh granules was 95.1%, and Bulk Density was 57.9 pcf.

For the other half of trial batch 5D (cured wet for 3 days at 100 F and then dried at 240 F), moisture loss in the granules was 8.9% (compared to an estimated moisture content of 14.7% following granulation). RTA for the 10×16 mesh granules was 97%, and Bulk Density was 60.2 pcf.

For trial batch B, after 5 days wet curing time at room temperature and drying at 240 F, moisture loss in the granules was 20% (compared to an estimated moisture content of 26% following granulation). RTA for the 10×16 mesh granules was 93%, and Bulk Density was 38 pcf.

For trial batch C, one third of the granules were wet cured for 4 hours, one third for 20 hours, one third for 3 days—all at room temperature.

For the portion of trial batch C wet cured for 4 hours at room temperature and dried at 240 F, moisture loss in the granules was 22.9% (compared to an estimated moisture content of 24% following granulation). RTA for the 10×16 mesh granules was only 24%.

For the portion of trial batch C wet cured for 20 hours at room temperature and then dried at 240 F, moisture loss was 19.8% (compared to an estimated moisture content of 24% following granulation). RTA for the 10×16 mesh granules increased to 92%.

For the portion of trial batch C wet cured for 3 days at room temperature and then dried at 240 F, moisture loss was 19.4% (compared to an estimated moisture content of 24% following granulation). RTA for the 10×16 mesh granules increased to 96%, and Bulk Density was 43 pcf.

Table II shows the recipe and dry granule properties for 3 trial batches prepared in the laboratory which included perlite as a lightweight additive.

For trial batches 13D and 13E, the perlite ingredient was thoroughly mixed into a homogeneous mixture of dried dolomite and Portland cement, and this mixture was then added to the "initial water" with mechanical mixing sufficient to wet and thoroughly blend all the ingredients within 5 seconds. For trial batch 13A.1, the perlite ingredient was first blended with the dried dolomite and this dry mixture was added to a Portland cement and water slurry with mechanical mixing sufficient to wet and thoroughly blend all the ingredients within 5 seconds. The initial mixing of dry and wet ingredients was completed in the laboratory with a hand mixer fitted with traditional "flat blade" metal beaters and ~2 quart stainless steel mixing bowl. This procedure simulated initial mixing in a commercial pin mixer.

Following the initial blending of dry ingredients and the water solution, granulation continued in the same bowl, using a hand mixer with spiral wire beaters and fine water spray added from a hand held spray bottle, until a majority of the particles attained the desired size, which in these trial batches was 8×16 mesh. This procedure further simulated the granulation which would occur in a commercial pin mixer.

Following granulation with the hand mixer, the entire batch was tumbled for approximately one minute (~25 revolutions) in a 16 inch diameter by 3.5 inch deep pelletizing pan (inclined at 45° above horizontal) to improve the roundness of the granules and provide a better estimate of granule properties if the granules would be produced in a commercial pin mixer/pelletizing pan process.

Following granulation and initial "green pellet" bulk density determination, each trial batch was stored in a sealed container, maintained at room temperature for the time period shown in Table II and then placed and spread into a ½ inch thick layer in a ~12×22 aluminum pan for drying at room temperature (~75° F.; ~50% relative humidity (RH)). After 3 days drying, the % moisture loss for the three batches ranged from 16.9% to 18.9%. The 8×16 mesh granules were collected from each batch by sieving. RTA for the 8×16 mesh granules ranged from 83% to 90.1% and bulk density ranged from 38.6 pcf to 48.7 pcf.

Table III shows the recipe and dry granule properties for trial batch 8A-1 prepared in the laboratory and cured by "Re-Hydration".

For trial batch 8A-1, the Portland cement ingredient was thoroughly mixed into a homogeneous mixture of dried dolomite and particle board flour, and this dry mixture was then added to the "initial water" with mechanical mixing sufficient to wet and thoroughly blend all the ingredients within 5 seconds. The initial mixing of dry and wet ingredients was completed in the laboratory with a hand mixer fitted with traditional "flat blade" metal beaters and ~2 quart stainless steel mixing bowl. This procedure simulated initial mixing in a commercial pin mixer.

Following the initial blending of water with the dry ingredients, granulation continued in the same bowl, using a hand mixer with spiral wire beaters and fine water spray added from a hand held spray bottle, until a majority of the particles attained the desired size, which for this trial batch was 8×16 mesh. This procedure further simulated the granulation which would occur in a commercial pin mixer.

Following granulation with the hand mixer, the entire batch was tumbled for approximately one minute (~25 revolutions) in a 16 inch diameter by 3.5 inch deep pelletizing pan (inclined at 45° above horizontal) to improve the roundness of the granules and provide a better estimate of granule properties if the granules would be produced in a commercial pin mixer/pelletizing pan process.

Following granulation and initial "green pellet" bulk density determination, the trial batch was stored in a sealed container maintained at room temperature (that is, "wet cured") for 20 hours and then placed and spread into a ~½ inch thick layer in a ~12×22 aluminum pan for drying at room temperature (~75° F.; ~50% relative humidity (RH)).

TABLE II

Examples Using Perlite as Lightweight Agent

|  |  | Batch Number | | |
| --- | --- | --- | --- | --- |
|  |  | 13D | 13E | 13A.1 |
| Ingredients % of Dry Granule Composition | Type III Portland Cement (St. Marys - Detroit) | 20 | 21 | 20 |
|  | #60 Dried Dolomite (Carey, OH, ~90% pass 100M; ~65% pass 200 Mesh) | 65 | 69 | 70 |
|  | Perlite (Dicalite Minerals HP2000, microspheres) mean particle diameter = 50-60m micron | 15 |  |  |
|  | Perlite (Dicalite Minerals HP100) mean particle diameter = 300 micron |  | 10 |  |
|  | Perlite (Dicalite Minerals crushed Perlite 476/FF76) |  |  | 10 |
| Batch Granulation | Dry Materials - (thoroughly mixed) - grams | 600 | 570 | 480 |
|  | Portland cement (Type III) Grams of Dry Cement PC Type III was added as a slurry . . . (120 gr cement blended with 167.5 gr water) |  |  | 120 |
|  | Initial Water Blended Rapidly with Dry Materials - grams | 101.7 | 150 | 167.5 |
|  | Water added during mixing bowl granulation - Grams | 99.7 | 64.6 | 16 |
|  | Water added during pan granulation - Grams Following Granulation | 0 | 0 | 0 |
|  | Green Pellet Moisture Content (Calculated) % | 25.2 | 27.5 | 23.5 |
|  | Green Pellet Bulk Density (pcf) | 49.8 | 42.6 | 50.7 |
|  | Weight % Yield for 8 × 16 mesh pellets (after drying) Approx | 45 | 30 | 34 |
| Batch Curing and Dry Granule Properties | Time Period Granules were Stored Wet at Room Temperature | 20 hours | 2 days | 20 hours |
|  | All tests on 8 × 16 Fraction (After Dried for 3 Days at ~75 F.; 50% RH) |  |  |  |
|  | Moisture Loss (%) | 17.9 | 18.9 | 16.9 |
|  | Bulk Density (pcf) | 45.8 | 38.6 | 48.7 |
|  | % Resistant to Attrition (RTA) | 89.3 | 90.1 | 83 |

After 3 days drying, % moisture loss was 22%, bulk density for 8×16 mesh granules was 39.1 pcf, and RTA for 8×16 mesh granules was 82.4%.

Two "sub-samples" of the 8×16 mesh air dried 8×16 mesh granules were cured further by "re-hydration".

The first "sub-sample"—a fifty gram portion of the 8×16 mesh air dried granules—was stored at room temperature in a high humidity (~95% RH) chamber for 44 days. These granules "re-hydrated by exposure to high humidity" were then dried for 3 days at room temperature (~75° F.; ~50% RH). Following drying at room temperature, the sample weighed 52.9 grams (suggesting 2.9 grams of moisture was absorbed by the sample). The bulk density was 41.8 pcf and the RTA was 93.4%.

The second "sub-sample" of the trial batch—a 66 gram portion of the air dried 8×16 mesh granules—was re-wetted with 8.8 grams of water and stored at room temperature in a sealed container for 40 days. These granules "re-hydrated by direct moisture addition" were then dried for 3 days at room temperature (~75° F.; ~50% RH). Following drying at room temperature, the bulk density was 41.1 pcf and the RTA was 95.2%.

Following granulation with the hand mixer, the entire batch was tumbled in a 16 inch diameter by 3.5 inch deep pelletizing pan (inclined at 45° above horizontal and rotating at ~25 RPM). Additional fine water spray was added from a hand held spray bottle until a majority of the particles attained the desired size which for these trial batches was 8×16 mesh. (Granulation in the pelletizing pan also improves the roundness of the granules and provides a better estimate of granule properties if the granules would be produced in a commercial pin mixer/pelletizing pan process.)

Following granulation and initial "green pellet" bulk density determination, each trial batch was stored in a sealed container maintained at room temperature (that is, "wet cured") for 5 hours (or 20 hours or 4 days depending on the batch—the wet curing time period for each batch is shown in Table VI) and then placed and spread into a ~½ inch thick layer in a ~12×22 aluminum pan for drying at room temperature (~75° F.; ~50% relative humidity (RH)). After 3 days drying, % moisture loss for each batch of granules ranged from 24% to 29.8%. The 8×16 mesh granules for each batch were captured by sieving and tested for bulk

TABLE III

Trial Batch Cured by "Re-Hydration"

| | | Batch Number 8A-1 |
|---|---|---|
| Ingredients % of Dry Granual Composition | Type III Portland Cement (St. Marys - Detroit) | 35 |
| | Particle Board Flour (Minus 35 mesh; ~8% Moisture) | 19.8 |
| | #60 Dried Dolomite (Carey, OH, ~90% pass 100M; ~65% pass 200 Mesh) | 45.2 |
| Batch Granulation | Dry Materials - (thoroughly mixed) - grams | 600 |
| | Initial Water Blended Rapidly with Dry Materials - grams | 228.1 |
| | Water added during mixing bowl granulation - Grams | 28.5 |
| | Water added during pan granulation - Grams | 0 |
| | Following Granulation | |
| | Green Pellet Moisture Content (Calculated) % | 31 |
| | Green Pellet Bulk Density (pcf) | 42.6 |
| | Weight % Yield for 8 × 16 mesh pellets (after drying) Approx | 42 |
| Intial Batch Curing Prior to Curing by "Re-Hydration" | Time Period Pellets were Stored Wet at Room Temperature | 20 hours |
| | All tests on 8 × 16 Fraction (After Dried for 3 Days at ~75 F.; 50% RH) | |
| | Moisture Loss (%) | 22 |
| | Bulk Density (pcf) | 39.1 |
| | % Resistant to Attrition (RTA) | 82.4 |

Tables IV, V, and VI show the % composition, batch granulation details, and batch curing and granule properties, respectively, for eleven additional examples prepared in the laboratory and cured by re-hydration.

For each batch the mixture of dry ingredients was added to the "initial water" with mechanical mixing sufficient to wet and thoroughly blend all the ingredients within 5 seconds. The initial mixing of dry and wet ingredients was completed in the laboratory with a hand mixer fitted with traditional "flat blade" metal beaters and ~2 quart stainless steel mixing bowl. This procedure simulated initial mixing in a commercial pin mixer.

Following the initial blending of water with the dry ingredients, granulation continued in the same bowl using a hand mixer with spiral wire beaters and fine water spray added from a hand held spray bottle until the particles began to form small granules, which for these trial batches was approximately 8×50 mesh. This procedure further simulated the granulation which would occur in a commercial pin mixer.

density and RTA. Bulk density for ranged 30.1 pcf to 38 pcf, and RTA ranged from 37.4% to 78.4%. (The values for % moisture loss, bulk density, and RTA for each of the eleven additional example batches are shown in Table VI.)

A portion of the 8×16 air dried granules for each batch (either 80 grams or 100 grams depending on the batch) was re-wetted (that is, "re-hydrated by direct moisture addition"). The moistened granules were stored at room temperature in a sealed container for 24-30 days and then dried for 3 days at room temperature (~75° F.; 50% RH). Following drying at room temperature, the bulk density for each batch of granules ranged from 33.5 pcf to 41.9 pcf, and the RTA ranged from 80.2% to 95.9%.

The 8×16 mesh granules from three of the batches (trial batches 11G-1, 11G-2, and 10A) were further dried at 240 F. Moisture loss following the additional drying ranged from 3.9% to 6.1%. These granules showed bulk density values ranging from 34.7 pcf to 40.3 pcf and RTA values ranging from 80.5% to 89.3%.

TABLE IV

% COMPOSITION FOR ADDITIONAL EXAMPLES

| | | Batch Number | | | | |
|---|---|---|---|---|---|---|
| | | 8 + PBF-2.2 | 8 + PFB-1.1 | 8HWD.1 | 8CKD 2.1 | 8CKD 2.2 |
| Ingedients - % of Dry Granule Composition | Type III Portland Cement (St. Marys - Detroit) | 35 | 35 | 35 | 17.5 | 17.5 |
| | Type I Portland Cement (St. Marys - Detroit) | | | | | |
| | Ground Granulated Blast Furnace Slag (St. Marys) | | | | 10.5 | 10.5 |
| | Cement Kiln Dust (Lafarge - Alpena) | | | | 7 | |
| | Cement Kiln Dust (Lafarge - Paulding) | | | | | 7 |
| | Fly Ash (Portland cement commercial additive) | | | | | |
| | CIMENT FONDU ® (Kernoes Aluminate Technologies) (Added to PBF - See Table V) | | | | | |
| | Sodium Silicate (NaSiO2) solids (Added to PBF - see Table V) | | | | | |
| | Calcium Nitrate (ASTM C494 Type C - POLARSET ®) Calcium Nitrate Solids | | | | | |
| | Particle Board Flour (Sauder - Minus 35 mesh; ~8% Moisture) | 24 | 24 | | 19.8 | 19.8 |
| | Pulverized Wood Dust (Hardwood - Minus 35 mesh) | | | 19.8 | | |
| | #60 Dried Dolomite, Carey, OH ~90% pass 100M and ~65% pass 200 Mesh) | | 41 | 45.2 | 45.2 | 45.2 |
| | 50/50 Blend #60 & #30 Dried Dolomite, Carey, OH ~75% pass 100M and ~40% pass 200 Mesh) | 41 | | | | |

| | | Batch Number | | | | | |
|---|---|---|---|---|---|---|---|
| | | 8FA.1 | 8CaN.3 | 11G-1 | 11G-2 | 11D-1 | 10A |
| Ingedients - % of Dry Granule Composition | Type III Portland Cement (St. Marys - Detroit) | 17.5 | 7 | 35 | 28 | 31.5 | 17.5 |
| | Type I Portland Cement (St. Marys - Detroit) | | 27.5 | | | | |
| | Ground Granulated Blast Furnace Slag (St. Marys) | 10.5 | | | 7 | 3.5 | 17.5 |
| | Cement Kiln Dust (Lafarge - Alpena) | | | | | | |
| | Cement Kiln Dust (Lafarge - Paulding) | | | | | | |
| | Fly Ash (Portland cement commercial additive) | 7 | | | | | |
| | CIMENT FONDU ® (Kernoes Aluminate Technologies) (Added to PBF - See Table V) | | | | | 5.1 | |
| | Sodium Silicate (NaSiO2) solids (Added to PBF - see Table V) | | | 0.9 | 0.9 | | |
| | Calcium Nitrate (ASTM C494 Type C - POLARSET ®) Calcium Nitrate Solids | | 1.4 | | | | |
| | Particle Board Flour (Sauder - Minus 35 mesh; ~8% Moisture) | 19.8 | 19.5 | 19.8 | 19.8 | 19.8 | 19.8 |
| | Pulverized Wood Dust (Hardwood - Minus 35 mesh) | | | | | | |
| | #60 Dried Dolomite, Carey, OH ~90% pass 100M and ~65% pass 200 Mesh) | 45.2 | 44.6 | 44.3 | 44.3 | 40.1 | 45.2 |
| | 50/50 Blend #60 & #30 Dried Dolomite, Carey, OH ~75% pass 100M and ~40% pass 200 Mesh) | | | | | | |

TABLE V

BATCH GRANULATION FOR ADDITIONAL EXAMPLES

| | | Batch Number | | | | | | | | | | | |
|---|---|---|---|---|---|---|---|---|---|---|---|---|---|
| | | 8 + PBF-2.2 | 8 + PFB-1.1 | 8HWD.1 | 8CKD 2.1 | 8CKD 2.2 | 8FA.1 | 8CaN.3 | 11G-1 | 11G-2 | 11D-1 | 10A |
| Batch Granulation | Total Quantity of Dry Materials - (thoroughly mixed) - grams<br>Note: Ingredients were blended into the dry mixture in the following order:<br>(1) Dried Dolomite<br>(2) PBF (or Wood Dust)<br>(Including PBF treated with Sodium Silicate or Ciment Fondu)<br>(3) GGBFS (Slag) (if added)<br>(4) CKD (if added)<br>(5) Fly Ash (if added)<br>(6) Portland cement | 600 | 600 | 600 | 600.3 | 600.3 | 600 | 600 | 600 | 600 | 600 | 600 |
| | Particle Board Flour Treated with Sodium Silicate Solution (Grams)<br>Note: The 124.4 gr of PBF treated with sodium silicate provides 118.8 gr (19.8%) of PBF and 5.6 gr (0.9%) of sodium silicate solids<br>Procedure for preparing PBF treated with sodium silicate:<br>A solution containing 5gr sodium silicate in 50gr water was made by mixing 13.3 gr of sodium silicate solution (37.5% solids) with 41.7 gr water. The solution was sprayed and thoroughly blended into dry, bulk PBF (to attain a sodium silicate dry solids "loading" of 5 gr/100 grams of PBF) and then dried at 240 F. prior to being blended with the dried dolomite ingredient. | | | | | | | | 124.4 | 124.4 | | |
| | Particle Board Flour Treated with Ciment Fondu (Grams)<br>Note: The 158.5 gr of PBF treated with Ciment Fondu provides 118.8 gr (19.8%) of PBF and 30.7 gr (5.1%) of Ciment Fondu solids and 9 grams of chemically combined water<br>Procedure for preparing PBF treated with Ciment Fondu @:<br>A 310 gr sample of PBF was wetted with 150 grams of water, then 80 grams of Ciment Fondu powder was thoroughly blended in, and the damp mix was allowed to sit in a sealed container for 24 hrs and then air dried for 2 days. Weight of the mixture after 2 days air drying = 414 GR. | | | | | | | | | | 158.5 | |
| | Initial Water (grams) Blended Rapidly with Dry Materials<br>Calcium Nitrate Solution - ( POLARSET ®)<br>Liquid Grams included with Initial Water Addition | 253 | 228 | 212.8 | 180.7 | 181.6 | 190 | 193.7<br>37 | 199.6 | 202 | 191.8 | 201 |
| | Water added during mixing bowl granulation - Grams<br>Water added during pan granulation - Grams | 37.8<br>55.2 | 64.3<br>39.7 | 23.4<br>33.1 | 47.3<br>67.89 | 63.6<br>43.8 | 33.8<br>59.3 | 22.6<br>34.1 | 23.6<br>65.4 | 23.1<br>68.3 | 20.1<br>40 | 24<br>39.3 |
| | Following Granulation<br>Green Pellet Moisture Content (Calculated) %<br>Green Pellet Bulk Density (pcf)<br>Weight % Yield for 8 x 16 mesh pellets (after drying) Approx | 37.6<br>39.2<br>66 | 36.7<br>40.3<br>58 | 32<br>42.4<br>63 | 33.8<br>41.8<br>70 | 33.3<br>42.8<br>70 | 32.9<br>41.2<br>63 | 32.3<br>41.8<br>60 | 33.4<br>41.7<br>45 | 33.8<br>40.1<br>45 | 31.3<br>42<br>57 | 31.6<br>42.8<br>55 |

TABLE VI

BATCH CURING AND GRANULE PROPERTIES FOR ADDITIONAL EXAMPLES

| | | Batch number | | | | |
|---|---|---|---|---|---|---|
| | | 8 + PBF-2.2 | 8 + PFB-1.1 | 8HWD.1 | 8CKD 2.1 | 8CKD 2.2 |
| Batch Curing | Initial Wet Storage/Curing Time for "Green Pellets" (Time Period Starts Immediately Following Granulation) (At Room Temperature) | 5 Hours | 5 Hours | 5 Hours | 5 Hours | 5 Hours |
| | All tests on 8 × 16 Fraction of Cured and Dried Granules | | | | | |
| | Test Results for 8 × 16 mesh granules following the initial wet storage/curing period followed by 3 days drying at ~75 F.; ~50% RH | | | | | |
| | Moisture Loss (%) | 29.8 | 28.4 | 23.9 | 27.4 | 26.6 |
| | Bulk Density (pcf) | 31.2 | 30.1 | 38 | 35.3 | 35.7 |
| | % Resistant to Attrition (RTA) | 71.8 | 69 | 78.4 | 37.4 | 58.6 |
| | Re-Hydration for 8 × 16 mesh granules | | | | | |
| | Grams of granules selected for additional curing | 80 | 100 | 100 | 80 | 80 |
| | Grams of water added to "re-hydrated" granules for additional curing | 15 | 18 | 18 | 15 | 15 |
| | Test Results for 8 × 16 mesh "re-hydrated" granules following 24-30 days of additional damp storage followed by 3 days drying at ~75 F.; ~50% RH | | | | | |
| | Bulk Density (pcf) | 35.1 | 33.5 | 41.9 | 38.5 | 37.3 |
| | % Resistant to Attrition (RTA) | 90.6 | 87.2 | 95.9 | 91.2 | 89.2 |
| | % Moisture (Determined by drying in vacuum oven) | | | | | |
| | pH | | | | | |
| | Test Results for 8 × 16 mesh "re-hydrated" granules following 24-30 days of additional damp storage followed by 3 days drying at ~75 F.; ~50% RH FOLLOWED BY DRYING AT 240 F. | | | | | |
| | Bulk Density (pcf) | | | | | |
| | % Resistant to Attrition (RTA) | | | | | |
| | % Moisture Loss | | | | | |
| | pH | | | | | |

| | | Batch number | | | | | |
|---|---|---|---|---|---|---|---|
| | | 8FA.1 | 8CaN.3 | 11G-1 | 11G-2 | 11D-1 | 10A |
| Batch Curing | Initial Wet Storage/Curing Time for "Green Pellets" (Time Period Starts Immediately Following Granulation) (At Room Temperature) | 20 Hours | 5 Hours | 20 Hours | 4 Days | 2 Days | 20 Hours |
| | All tests on 8 × 16 Fraction of Cured and Dried Granules | | | | | | |
| | Test Results for 8 × 16 mesh granules following the initial wet storage/curing period followed by 3 days drying at ~75 F.; ~50% RH | | | | | | |
| | Moisture Loss (%) | 26.9 | 24.3 | 25.3 | 26.6 | 24 | 25.6 |
| | Bulk Density (pcf) | 36.4 | 37.8 | 33.8 | 33.1 | 36.8 | 37.1 |
| | % Resistant to Attrition (RTA) | 53.8 | 54.2 | 70.7 | 56.5 | 66.4 | 68.5 |
| | Re-Hydration for 8 × 16 mesh granules | | | | | | |
| | Grams of granules selected for additional curing | 100 | 100 | 100 | 100 | 100 | 100 |
| | Grams of water added to "re-hydrated" granules for additional curing | 18 | 18 | 18 | 18 | 18 | 18 |
| | Test Results for 8 × 16 mesh "re-hydrated" granules following 24-30 days of additional damp storage followed by 3 days drying at ~75 F.; ~50% RH | | | | | | |
| | Bulk Density (pcf) | 37.3 | 40.7 | 36.6 | 37.2 | 40.9 | 38.2 |
| | % Resistant to Attrition (RTA) | 80.2 | 86.8 | 88.1 | 85.5 | 84.8 | 85.3 |
| | % Moisture (Determined by drying in vacuum oven) | | | | | 5.7 | |
| | pH | | | | 9.52 | | |
| | Test Results for 8 × 16 mesh "re-hydrated" granules following 24-30 days of additional damp storage followed by 3 days drying at ~75 F.; ~50% RH FOLLOWED BY DRYING AT 240 F. | | | | | | |
| | Bulk Density (pcf) | | | 36.4 | 34.7 | | 40.3 |
| | % Resistant to Attrition (RTA) | | | 89.3 | 80.5 | | 82 |
| | % Moisture Loss | | | 6.1 | 4.7 | | 3.9 |
| | pH | | | 9.78 | | | 9.2 |

In accordance with the provisions of the patent statutes, the invention has been described in what is considered to represent its preferred embodiments. However, it should be noted that the invention can be practiced otherwise than as specifically illustrated and described without departing from its spirit or scope.

What is claimed is:

1. A granular substrate comprised of a plurality of granules, each granule being comprised of a mixture comprising an inert mineral component, a mineral cement, and a light weight additive to reduce the bulk density of each granule, the mixture comprising 15% to 42% mineral cement, and wherein each granule is non-dispersible in water.

2. The non-dispersible granular substrate of claim 1, wherein the inert mineral component is selected from the group consisting of dolomite, limestone, ground recycled concrete, and ground air cooled blast furnace slag.

3. The non-dispersible granular substrate of claim 1, wherein the inert mineral component is selected from the group consisting of dolomite and limestone.

4. The non-dispersible granular substrate of claim 1, wherein the inert mineral component is comprised of dolomite.

5. The non-dispersible granular substrate of claim 4, wherein the mineral cement is comprised of Portland cement.

6. The non-dispersible granular substrate of claim 1, wherein the mineral cement is comprised of calcined lime and clay.

7. The non-dispersible granular substrate of claim 1, wherein the mineral cement is selected from the group consisting of Portland cement, finely ground Portland cement clinker, cement kiln dust, blends of Portland cement blends and one or more other cementitious material, and rapid-hardening hydraulic cements.

8. The non-dispersible granular substrate of claim 1, wherein the mineral cement is comprised of Portland cement.

9. The non-dispersible granular substrate of claim 1, wherein the mineral cement is comprised of Type III Portland cement.

10. The non-dispersible granular substrate of claim 1, wherein the light weight additive is selected from the group consisting of particle board flour, expanded silica, perlite, wood flour, cellulose, ground wheat straw, and diatomaceous earth.

11. The non-dispersible granular substrate of claim 1, wherein the light weight additive is selected from the group consisting of particle board flour and hard wood flour.

12. The non-dispersible granular substrate of claim 1, wherein the bulk density of the granules is 75 pounds per cubic foot or less.

13. The non-dispersible granular substrate of claim 1, wherein the granules exhibit an weight % resistance to attrition of 85% or more.

14. The non-dispersible granular substrate of claim 1, wherein the granules exhibit a liquid absorption capacity of 10% or more.

15. The non-dispersible granular substrate of claim 1, wherein each granule is formed from a batch mixture comprised of an inert mineral component, a mineral cement, and water.

16. The non-dispersible granular substrate of claim 1, wherein the plurality of granules have a particle size distribution of 6×60 mesh.

17. The non-dispersible granular substrate of claim 1, wherein the plurality of granules have a particle size distribution of 8×20 mesh.

18. The non-dispersible granular substrate of claim 1, wherein the plurality of granules have an angle of repose of 40° or less.

19. A method of making a non-dispersible granular substrate, comprising:
    forming a batch mixture comprised of an inert mineral component, a mineral cement, a light weight additive, and water; and
    co-pelletizing the batch mixture to form a plurality of granules, the resulting granules being non-dispersible in water and comprising 15% to 42% mineral cement.

20. The method of claim 19, wherein the inert mineral component is selected from the group consisting of dolomite and limestone, and the mineral cement is comprised of Portland cement.

21. The method of claim 19, further comprising the steps of drying the plurality of non-dispersible granules, then re-hydrating the granules, and then re-drying the granules.

22. The method of claim 19, wherein the batch mixture is a homogenous mixture.

23. A granular substrate comprised of a plurality of granules, each granule being comprised of a mixture comprising an inert mineral component, a mineral cement, and a light weight additive to reduce the bulk density of each granule, the mixture comprising 30% to 42% mineral cement, and wherein each granule is non-dispersible in water.

* * * * *